United States Patent
Nagamatsu

(12) 
(10) Patent No.: US 6,326,606 B2
(45) Date of Patent: Dec. 4, 2001

(54) METHOD AND APPARATUS FOR CHECKING SHAPE

(75) Inventor: Katsunori Nagamatsu, Tokyo (JP)

(73) Assignee: NEC Corporation, Tokyo (JP)

(*) Notice: Subject to any disclaimer, the term of this patent is extended or adjusted under 35 U.S.C. 154(b) by 0 days.

(21) Appl. No.: 09/736,435

(22) Filed: Dec. 15, 2000

Related U.S. Application Data

(62) Division of application No. 09/218,101, filed on Dec. 22, 1998, now Pat. No. 6,211,505.

(30) Foreign Application Priority Data

Dec. 25, 1997 (JP) .................................... 9-357864
Jul. 27, 1998 (JP) .................................... 10-211567

(51) Int. Cl.⁷ ............................ H01J 40/14; G01B 11/00
(52) U.S. Cl. ...................... 250/214 R; 250/237 R; 382/144; 356/388
(58) Field of Search .......................... 250/214 R, 214 A, 250/214 AG, 214 DC, 216, 205, 237 R, 559.2; 382/141, 144; 356/388, 601, 239.1, 239.3

(56) References Cited

U.S. PATENT DOCUMENTS 5,012,523 * 4/1991 Kobayashi et al. .................. 382/145
5,572,598    11/1996 Wihl et al. .

FOREIGN PATENT DOCUMENTS

| 0 132 122 A2 | 1/1985 | (EP) . |
|---|---|---|
| 0 532 927 A2 | 3/1993 | (EP) . |
| 0 628 806 A2 | 12/1994 | (EP) . |
| 2 076 533 A | 12/1981 | (GB) . |
| 63-56702 | 11/1988 | (JP) . |
| 64-3050 | 1/1989 | (JP) . |
| 4-362789 | 12/1992 | (JP) . |
| 5-46747 | 2/1993 | (JP) . |
| 6-139396 | 5/1994 | (JP) . |
| 10-97053 | 4/1998 | (JP) . |

* cited by examiner

Primary Examiner—John R. Lee
Assistant Examiner—Kevin Pyo
(74) Attorney, Agent, or Firm—Sughrue, Mion, Zinn, Macpeak & Seas, PLLC

(57) ABSTRACT

The level of a laser beam is controlled to the maximum level detectable by a sensor, and light transmitted through the pattern is normalized with branched light. The laser beam level is made up for variations, and noise at zero and saturation levels are removed. Data thus can be taken out, in which noise in edge portions is always at a constant level. It is thus possible to increase the pattern image accuracy and obtain sharper image.

5 Claims, 10 Drawing Sheets

METHOD AND APPARATUS FOR CHECKING SHAPE

This is a divisional of application Ser. No. 09/218,101 filed Dec. 22, 1998, now U.S. Pat. No. 6,211,505, the disclosure of which is incorporated herein by reference.

BACKGROUND OF THE INVENTION

The present invention relates to an apparatus for and a method of shape checking patterns and, more particularly, to an apparatus for and a method of shape checking patterns requiring highly accurate pattern images such as mask patterns.

The present invention also relates to light-permeable area shape checking apparatuses and, more particularly, to a transmitting area shape checking apparatus for shape checking light-permeable areas of a mask pattern or the like by illumination thereof. The present invention may be suitably used for checking the edge shapes of, for instance, a reticule used in a photographic process in IC manufacture. Of course the present invention is suitably applicable to the shape check of not only reticules but also mask patterns for masking photo-sensitive resin or the like in a photo-etching technique in IC manufacture. Also, it is possible to apply the present invention not only to the IC manufacture but also to the shape check of mask members used for masking against light transmission. Furthermore, the present invention is suitably applicable not only to mask members but also to objects which can be checked by checking the light permeability.

Japanese Patent Disclosure No. 63-567021 shows an apparatus for and a method of shape checking patterns of the pertaining type. According to this disclosure, a pattern is illuminated to obtain transmitted light therefrom with CCD or like sensor, and data obtained therefrom is checked by comparison as to whether it has a desired pattern.

In the shape check of a photo-mask used for drawing an integrated circuit pattern which requires super-high shape accuracy, two-dimensional deviations and distortions which arise between and in the photo-mask pattern and the obtained pattern data due to various causes pose problems.

There were techniques seeking to meet the required accuracy by measuring beforehand deviations and distortions generated in pattern data, correcting the deviations and distortions according to the result of measurement and making the pattern comparison with the corrected pattern data.

The above prior art pattern shape check apparatus had a problem that variations of light from the pattern, variations of the incident light quantity and secular variations of detecting means reduce the pattern shape recognition accuracy, thus reducing the sharpness of image. To solve this problem, the applicant earlier developed a technique disclosed in Japanese Patent Application No. 9-357846, which will now be described.

Like the technique described above, a pattern is illuminated, but the illuminating light is partly used for the level detection thereof. The individual branch light beams are detected by respective CCD sensors or the like. These signals contain components representing illuminating light level variations. For correcting these signals, the branched light for the level detection is amplified to the same level as the detected level of directly transmitted illuminating light, in the light obtained from the pattern, and the amplified light is used to divide the light obtained from the pattern.

More specifically, the illuminated light level variations to the pattern in dependence on the incidence position are normalized (to a constant level) by using the amplified light which includes the level variations to correct the illuminated light level variations. It is thus possible to make utmost use of the illuminated light level range detectable by the sensor although the illuminating light level may be reduced.

This technique, as will be described later in the description of the embodiment, permits removal of noise at zero level and maximum level of the signal by A/D converting the normalized signal after providing offsets for an upper and a lower portions of the signal. Even in this case, however, a commonly termed edge portion of signal between the detected levels of zero and maximum contains noise. This noise is dependent on the level of light transmitted through the pattern before the correction. Therefore, the noise level is varied whenever the light level is varied. For this reason, the pattern shape recognition accuracy is reduced with reducing illuminating light level, which is a first problem of the prior art technique.

In summary, the problem posed in conventional pattern shape recognition is that variations of light from a pattern to be checked, illuminating light level variations and variations of detecting means in long use results in reduced accuracy of the pattern shape recognition and reduced sharpness of image.

Heretofore, the shape check of an object is made by comparing an image of the object with a reference image. The reference image is obtained by picking up the good sample of the subject or generated from CAD data or the like. The two images are compared after binalizing them. For example, Japanese Patent Disclosure No. 5-46747 discloses a method of obtaining binalized images of wiring patterns of printed circuit boards.

However, edge areas of an object can not be satisfactorily checked by comparing two images. In the meantime, by comparing an image of an object and the reference image as multiple-value data such as 256 gradation data, satisfactory comparison of the rising falling state of edge areas can be obtained, thus permitting satisfactory shape check.

In a different method of shape check, a CPU or a program is used. In this case, light emitted from a light source and transmitted through an object is photoelectrically converted in a CCD sensor or the like. In this case, the capacity of the light source such as a laser and the sensor is subject to changes in long use. After long use, therefore, it is no longer possible to obtain satisfactory comparison of the object image with the reference image. To evade influence of the secular changes in the capacity of the laser, the laser beam is split, and the ratio or the difference between light transmitted through an object and light not transmitted therethrough is calculated.

However, even by splitting the laser beam and calculating the ratio between the light transmitted through an object and the light not transmitted therethrough, the measurement errors due to the sensor and associated analog circuit can not be removed. Neither it is impossible to remove influence of noise generated in the sensor and following analog circuit.

In the case of checking the edge areas from gradation changes in the rising and falling, the image gradation is desirably not changed with pattern areas free from changes.

However, changes in the image gradation occurs even with pattern areas free from changes due to shot noise in the sensor, measurement errors in the A/D converter and noise in the following analog circuit. These changes result in accuracy reduction in the comparison of the object image with reference image or like process.

More specifically, the prior art arrangement with the setting of the level of light transmitted through the pattern to be the maximum level and the level of light not transmitted through the pattern to be the minimum level, has a drawback that the maximum and minimum level areas are unstable, which is a second problem of the prior art technique.

SUMMARY OF THE INVENTION

The present invention therefore seeks to solve the above first problem, specifically it has an object of providing an apparatus for and a method of shape checking patterns, capable of obtaining more accurate and sharper image patterns.

The present invention also seeks to overcome the above second problem in the prior art, and its specific object is to provide a light-permeable area shape check apparatus, which permits satisfactory shape check of mask patterns or like objects having light-permeable areas.

According to the present invention, the illuminating means emits illuminating light, the illuminating beam splitting means illuminates the pattern by receiving the illuminating light, and also produces branched light therefrom for detecting the level of the illuminating light. The illuminating beam splitting means illuminates the pattern, the pattern light detecting means receives the light from the pattern and detects the level of the received light, while also controlling the illuminating light such that the detected level is always a predetermined level and supplying an electric signal obtained by converting the controlled light.

Also, the illuminating beam splitting means produces the branching light from the received illuminating light, and the light detecting means receives the branched light and detects the level thereof, while also controlling the branched light such that the detected level is always a predetermined level and supplying an electric signal obtained by converting the controlled light.

The pattern light detecting means and the light detecting means supply their respective output signals, and the correcting means corrects the output signal of the pattern light detecting means by dividing this signal by the output signal of the light detecting means, and supplies a signal containing noise at a constant level. The correcting means supplies the constant noise level signal, and the pattern recognizing means recognizes the pattern according to this output signal.

The meaning of the correction of the output signal of the pattern light detecting means by dividing this signal by the output signal of the light detecting means is as follows.

Like the prior technique developed by the applicant, the output signal of the light detecting means is intrinsically a superimposition of the detected illuminating light and accompanying noise, and is used to normalize the output signal of the pattern light detecting means.

Thus, when the output signal of the pattern light detecting means is normalized with the output signal at the same level, it is expanded, and also the illuminating light level variations are corrected. The maximum level of this signal is thus the maximum level of the level detection range of the sensor, and the sensor can detect the signal over its entire level detection range even with possible reduction of the illuminating light level.

Since the pattern light detecting means and light detecting means always control the output of the illuminating light and the branched light to predetermined levels, it is possible to estimate the noise levels of shot noises in these detecting means and associated analog circuits to be constant.

In the present invention, a pattern shape checking apparatus is provided, which can reduce noise level for obtaining more accurate and sharper images.

When the illuminating light level is reduced so that the transmitted light level is below the maximum level of the pattern light detecting means, the transmitted light level is corrected to reach the maximum level of the pattern light detecting means.

For the normalization of the output signal of this pattern light detecting means, the light detecting means also controls the maximum level of the received light to the maximum level detectable by it, i.e., to the same level as the corrected output of the pattern light detecting means.

As will be described later in detail, when the same detector detects the same pattern, the higher the output signal level, the obtained image has the more clear contrast and is the more accurate and the sharper. That is, the higher the output signal level, the noise level is the lower.

As described above, the signal level of the pattern light detecting means is normalized with the signal of the light detecting means, which is made to the same in level.

In the present invention, the normalization is performed with the signal of the light detecting means, which is made to be lower in level than the signal level of the pattern light detecting means. As a result, the signal level of the pattern light detecting means is expanded as a whole, and the maximum level of this signal exceeds the level detection range of the detecting means.

Since the noise in this signal is always at a fixed level as noted before, by setting the level in excess of the level detection range, obtained as a result of the expansion, to be more than the extent of the noise level, it is possible to completely remove the noise portion which is in excess of the level detection range.

In the present invention, an offset is set for the pattern shape checking apparatus in order to remove the noise contained in the light corresponding to the pattern portion through which the illuminating light is transmitted, i.e., the zero level portion of the output signal of the detecting means.

More specifically, after the sufficient expansion of signal, an offset is provided for subtraction from the corrected output signal to an extent that the noise level at the zero level of the detecting means does not exceed the zero level and that the noise level at the maximum level detectable by the detecting means does not exceed the maximum detectable level. As a result, the noise level outside the detectable range can be completely removed.

In the present invention, a specific example is provided, in which actual signal removal from the signal capable of removing noise is performed to obtain the data for the pattern recognition.

More specifically, the upper and lower limits of measurement of the A/D converter are made to be the maximum detectable level and the zero level of the detecting means, respectively, whereby it is possible to obtain the multi-image data, having values between the upper and lower limits of measurement, perfectly free from noise other than those of the "edge" portions. This image data is suitable for making a check using a computer or the like as to whether a desired pattern is obtained.

It will be readily understood that the method of reducing noise level by holding the light from the pattern and signal containing variation data of the illuminating light fixed, when normalizing the light from the pattern with the signal containing the illuminating light variation data, is not only applicable to actual apparatus but also capable of providing its function alone.

The method is not only actual apparatus but also effective as such.

According to other aspect of the present invention, light projected from the light source is transmitted or blocked by the object to be checked according to the pattern thereof. The first sensor photoelectrically converts light incident on it as a result of the transmission or blocking of light. Signal corresponding edges of the light-permeable areas of the pattern rises or falls with a slope according to the level distribution of the light from the light source and the diameter of the spot of light. By comparing the rising or falling state with that of a reference image, it is possible to satisfactorily extract the shape of the object, i.e., defects of the edges. However, when the output of the first sensor is converted by the A/D converter, the output thereof may contain much harmonic noise components, which are added in the analog circuit or the sensor, depending on the capacity of the light source or the sensitivity of the sensor. Particularly, harmonic noise component contained in a flat portion of output after rising or falling thereof, reduces the accuracy of the defect check.

The gain correcting means corrects, by changing the waveform of the output signal of the first sensor, the maximum output level of the first sensor to be above the upper light of measurement of the A/D converter and the minimum level of the output signal of the first sensor to be below the lower limit of measurement of the A/D converter. Thus, when the slope of the rising or falling becomes only slight, the maximum and minimum levels of the output of the first sensor get out of the capacity of the A/D converter, thus providing monotonous data. This means that the digital data in the shape check has a maximum or a minimum value for regions, which have continuous light-permeable or light-blocking areas and are so important. It is thus possible to obtain a pattern sampling image which can be readily processed, improve the accuracy of the shape check and further increase the speed of processing.

According to the present invention, it is also possible to satisfactorily adopt a structure, which removes noise contained in the light from the light source by taking the ratio between two sensors outputs. In the example of taking the two sensor outputs, a reference level of the output of one of the sensors is experimentarily obtained beforehand, and the output of the other sensor is corrected according to the ratio between the first sensor output level and the reference level. In this way, it is possible to obtain a pattern sampling image which can be readily processed.

Other objects and features will be clarified from the following description with reference to attached drawings.

PREFERRED EMBODIMENTS OF THE INVENTION

Preferred embodiments of the present invention will now be described with reference to the drawings.

Figure 1:
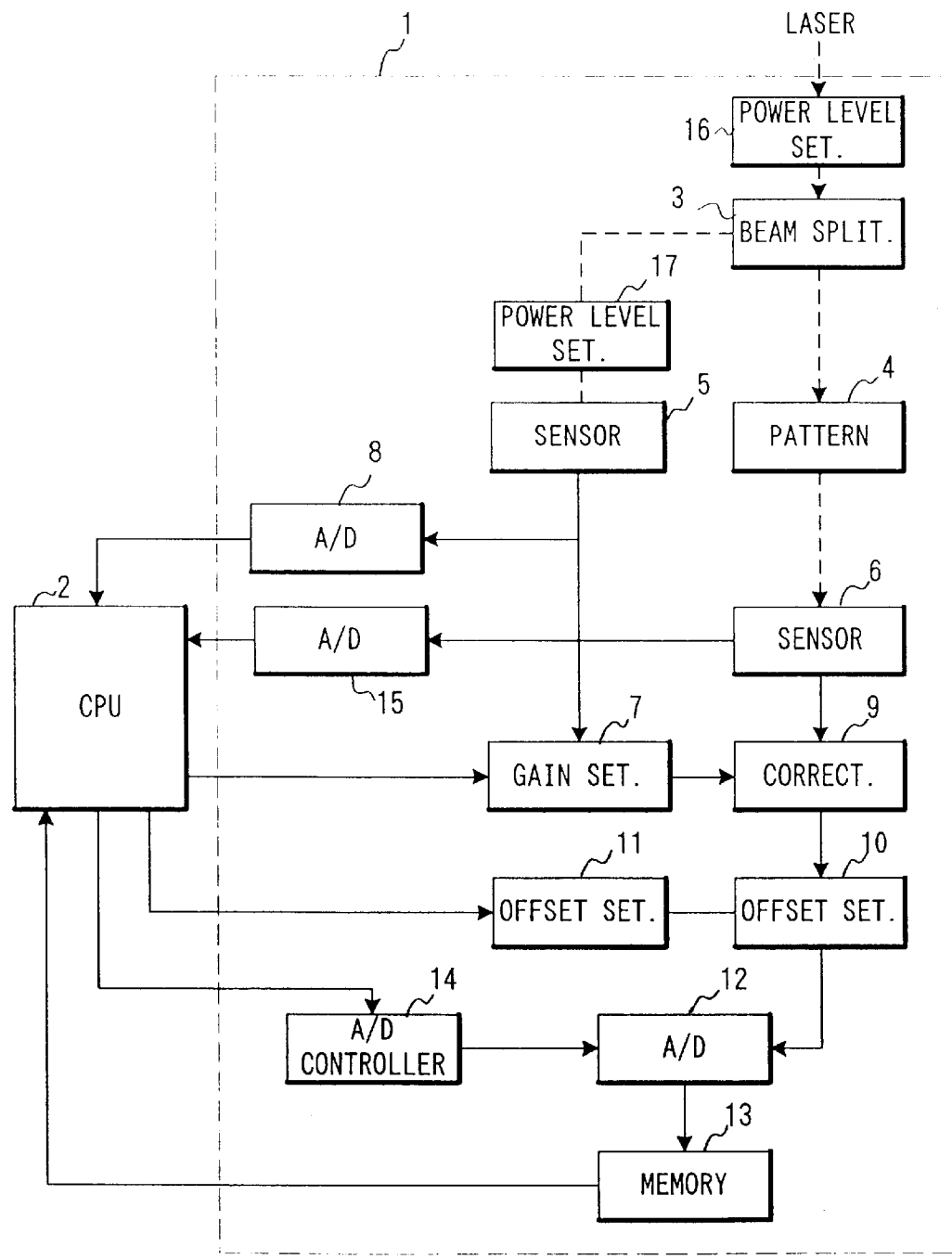
FIG. 1 is a block diagram showing an embodiment of the apparatus for shape checking patterns according to the present invention.

FIG. 1 is a block diagram showing an embodiment of the apparatus for shape checking patterns according to the present invention. Referring to the Figure, a pattern detection unit 1 has an optical path of illuminating light from a light source (not shown), which is formed by an optical system for pattern light detection including a power level setting means 16, a beam splitting means 3, a pattern 4 and a sensor 6. The beam splitting means 3 splits the illuminating light into two light beams, one led along the above optical path and the other led along a separate path. In the branched optical path a power level setting means 17 and a sensor are provided.

Illuminating light from the optical path (not shown) which is led along the optical path through the power level setting means 16 and the beam splitting means 3, illuminates the pattern 4, and branched light led along the separate optical path is led through another power level setting means 17 to a sensor 5. The beam splitting means 3 thus constitutes the illuminating light branching means noted above, while the light source (not shown) constitutes the illuminating means.

The sensor 6 is connected to an A/D converter 15 and a correcting circuit 9. The A/D converter 15 is connected to the CPU 2. The sensor 6 can convert the received light to an analog signal, and supply this analog signal to the A/D converter 15 and the correcting circuit 9. More specifically, when the sensor 6 receives illuminating light emitted from the light source (not shown) and transmitted through the pattern 4, it converts the received light to an analog signal, and supplies the analog signal to the A/D converter 15 and the correcting circuit 9.

The A/D converter 15 can convert the input signal, i.e., electric analog signal, to a digital signal, and supply the digital signal to the CPU 2. Thus, light received by the sensor 6 is coupled after digital conversion to the CPU 2.

The sensor 5, likewise, is connected to an another A/D converter 8 and also to a gain setting means 7. The A/D converter 8 is connected to the CPU 2. The sensor 5 can convert the received light to an analog signal, and supply the analog signal to the A/D converter and the gain setting means 7. That is, when the sensor 5 receives the branched light noted above, it converts the received light to an analog signal, and supplies the analog signal to the A/D converter 8 and the gain setting means 7. The A/D converter 8 can convert the input signal, i.e., electric analog signal, to a digital signal and supply the digital signal to the CPU 2. Thus, light received by the sensor 5 is coupled after digital conversion to the CPU 2.

The CPU 2 can detect the level of light received by the sensor 6 on the basis of the digital signal from the A/D converter 15, and responsive to this detection supplies a command to the power level setting means 16. According to this command, the power level setting means 16 controls the illuminating light output level to a predetermined level. Likewise, the CPU 2 can detect the level of light received by the sensor 5, according to the digital signal from the A/D converter 8, and responsive to this detection supplies a command to the power level setting means 17 for control thereby of the branched light output level to a predetermined level.

The power level setting means 16, the sensor 6, the A/D converter 15 and the CPU 2 thus constitute the pattern light setting means noted above, while the power level setting means 17, the sensor 5, the A/D converter 8 and the CPU 2 constitute the above light detecting means. The power level setting means 16 and 17, which amplify the light outputs as shown above, may specifically use optical attenuators for light output control by controlling the attenuation value.

The CPU 2 is connected to the gain setting means 7, which is in turn connected to the correcting circuit 9. The gain setting means 7 supplies the electric signal input from the sensor 5 with gains instructed by the CPU 2, to the correcting circuit 9. The correcting circuit 9 thus receives the two different analog signals, and it divides one of these signals by the other and supplies the resultant analog signal. More specifically, when the correcting circuit 9 receives the signals from the gain setting means 7 and the sensor 6, it divides the signal from the sensor 6 by the signal from the gain setting means 7 and supply the result to an offset setting circuit 10. The correcting circuit 9 thus constitutes a correcting means.

The gain setting means 7, which gives the gains instructed by the CPU 2 to the received signal, may use a variable amplifier capable of digitally setting gains, or an attenuator capable of being programmed or the like.

The setting means 10 is connected to the correcting circuit 9, an offset-setting means 11, and a further A/D converter 12. The CPU 2 is connected to the off-set setting means 11. The CPU 2 can calculate offsets according to shot noises in the sensors 5 and 6 and also noise levels in the analog circuits, and supplies the calculated result to the offset setting circuit 11.

The offset setting means 11 controls the offset setting circuit 10 on the basis of the received offset data from the CPU 2, thus giving an offset to the analog signal supplied to the offset setting circuit 10, which thus supplies a signal with the offset.to the A/D converter 12.

An A/D converter 12 is connected to the A/D converter 14, and a memory 13 connected in turn to the CPU 2. The A/D converter 12 converts the input analog signal to a digital signal under control of the A/D converter controller 14, and supplies the produced digital signal. More specifically, the A/D converter 12 converts the received signal from the offset setting circuit 10 to a digital signal, and supplies the digital signal to the memory 13.

The memory 13 stores the input signal, and also stores desired pattern data representing the shape of the pattern to be shape checked. The memory 13 stores the digital data noted above, and stores this data as multiple-value data of the pattern to be checked. The CPU 2 compares the data thus stored in the memory 13 with the desired pattern data having been stored therein beforehand.

The offset setting circuit 10, the offset setting means 11, the A/D converter 12, the A/D converter controller 14, the memory 13 and the CPU 2 thus constitute a pattern recognizing means. As the offset given here, the output signal waveform data from the correcting circuit 9 may be shifted as a whole only to the extent instructed from the CPU 2. The offset thus may be set by using a D/A converter or a programmable resistor, which supplies a voltage setting to an adder (or adder circuit).

Since it is sufficient that it can remove the fixed level noise present at 0 and maximum detected levels of signal, it is possible to replace the offsetting operation of the offset setting circuits 10 and 11 with an arrangement such that the A/D converter 12 produces a digital signal in a range free from the noise from the analog signal from the correcting circuit 9 under control of the A/D converter controller 14. As a further alternative, the memory 13 may be adapted to hold the digital signal from the A/D converter 12 so that a range free from the noise can be used in the pattern comparison.

Figure 12:
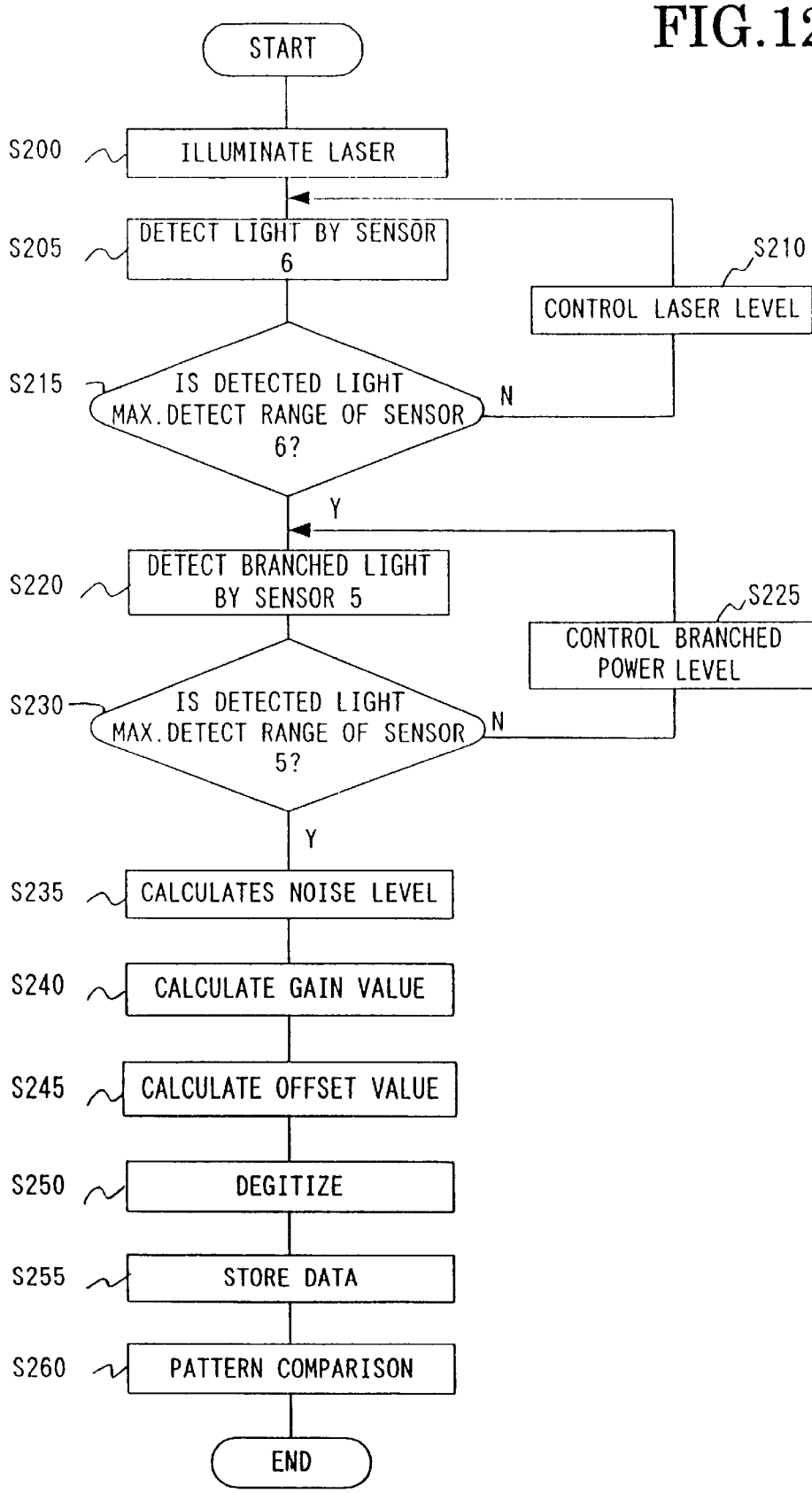
FIG. 12 shows a flow chart for describing the control by the CPU 2.

As described above, this embodiment of the pattern shape checking apparatus is controlled by the CPU 2. The control by the CPU 2 will now be described with reference to the flow chart of FIG. 12.

The pattern shape check is started with a step S200, in which a light source (i.e., a laser not shown) is caused to emit illuminating light, i.e., a laser beam. When the sensor 6 detects this illuminating light (step S205), the CPU 2 checks whether the signal representing the detected light reaches the maximum level of a level detection range of the sensor 6 (step S215). When it is not determined that the maximum level of the level detection range is reached, the power level setting means 16 controls the illuminating light such that the maximum level of the level detection range of the sensor 6 is reached (step S210).

The routine then returns to the step S205, and the above sequence of steps is repeatedly executed until it is determined in the step S215 that the illuminating light reaches the maximum level of the level detection range of the sensor 6. When it is determined that the maximum level of the level detection range is reached, the sensor 5 detects the branched light from the beam splitting means 3 (step S220), and the CPU 2 checks whether the branched light reaches the maximum level of a level detection range of the sensor 5 (step S230).

When it is not determined that the maximum level of the level detection range is reached, the power level setting means 17 controls the branched light such that the maximum level of the level detection range of the sensor 5 is reached (step S225). The routine then returns to the step S220, and the above sequence of steps is repeatedly executed until it is determined in the step S225 that the branched light reaches the maximum level of the level detection range of the sensor 5.

When the illuminating light has been controlled to the maximum level of the level detection range of the sensor 6 and also the branched light is controlled to the maximum level of the level detection range of the sensor 5, the CPU calculates the noise level (step 235). An example of the noise level calculation will now be described with reference to FIGS. 2 to 5.

Figure 2:
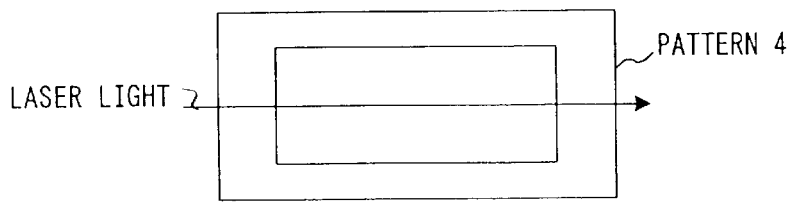
FIG. 2 shows a drawing representing manner in which a laser beam is transmitted through the pattern 4.
Figure 3:
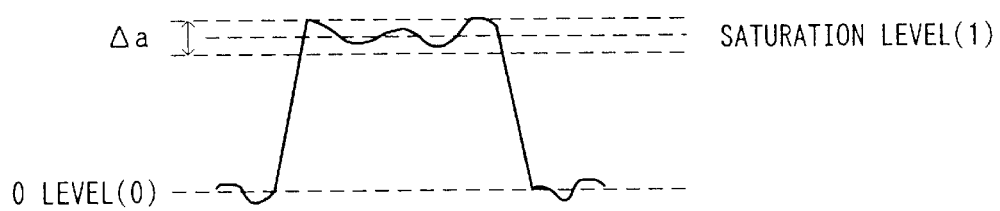
FIG. 3 shows the waveform of the output of the sensor 6 detecting the light transmitted through the pattern of FIG. 2.
Figure 4:
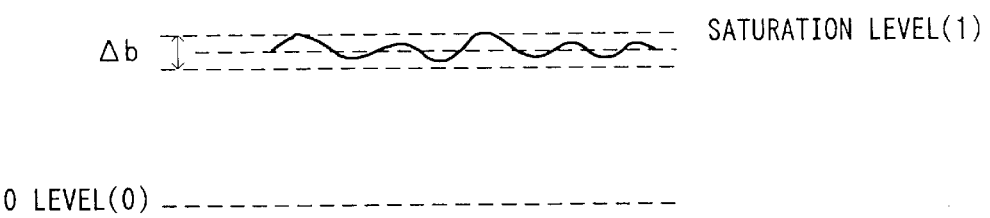
FIG. 4 shows the waveform of the output of the sensor 5.
Figure 5:
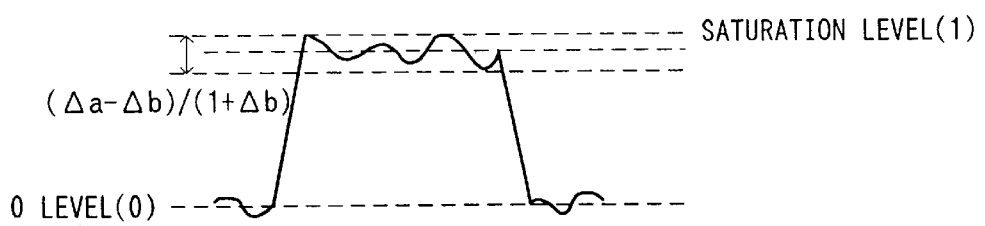
FIG. 5 shows the noise level after the correction of the present invention.

FIG. 2 shows the manner, in which a laser beam is transmitted through the pattern 4. FIG. 3 shows the waveform of the output of the sensor 6 detecting the light transmitted through the pattern. FIG. 4 shows the waveform of the output of the sensor 5. In FIGS. 3 and 4, for the sake of the brevity, the saturation level is labeled 1, the noise level of the shot noise of the sensor 6 and related analog circuit is labeled $\Delta a$, and the noise level of the shot noise of the sensor 5 and related analog circuit is referred to as $\Delta b$. The noise in the transmitting portions of the pattern 4 is calculated as:

$$(1+\Delta a)/((1+\Delta b)=1+(\Delta a-\Delta b)/(1+\Delta b)$$

where $(1+\Delta a)$ is the value of signal representing the light transmitted through the pattern 4, and $(1+\Delta b)$ is the value of signal representing the branched light corresponding to the position, at which $(1+\Delta a)$ is obtained. FIG. 5 shows the result of calculation. In the right side of the above equation, in which 1 represents the saturation level, $(\Delta a-\Delta b)/(1+\Delta b)$ represents the noise level.

The commonly termed "edge" portion which has a value between the zero and maximum detection levels of the sensor is, denoting the output level of the edge by m, is given as:

$$m(1+\Delta a)/(1+\Delta b)=m(1+(\Delta a-\Delta b)/(1+\Delta b)$$

where $m(1+\Delta a)$ is the signal value of the edge portion, and $(1+\Delta b)$ is the signal value of branched light corresponding to the position, at which $m(1+\Delta a)$ is obtained. In the above equation, in which m represents the output level of the edge, $m(\Delta a-\Delta b)/(1+\Delta b)$ represents the noise level.

For comparison, a method of noise level calculation in a technique, which was developed by the inventor and is disclosed in Japanese Patent Application No. 9-357864, will now be described. In this technique, the light incident on the pattern is partly amplified to the same level as the light transmitted through the pattern, and the light transmitted through the pattern is divided by the amplified light. This status is shown in FIGS. 9 to 11.

Figure 9:
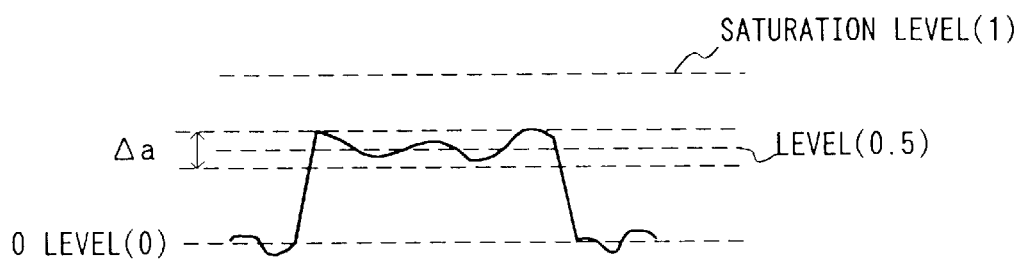
FIG. 9 shows the waveform of output light transmitted through a pattern like that shown in FIG. 2.
Figure 10:
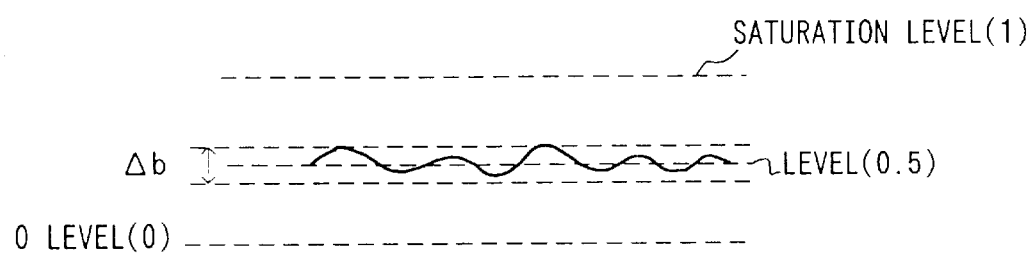
FIG. 10 shows the amplified output waveform of the branched light.

FIG. 9 shows the waveform of output light transmitted through a pattern like that shown in FIG. 2. In this case, unlike the present invention, the illuminating light is not controlled to the maximum detection level of sensor. Thus, as shown in FIG. 9, it may be the case that the output of the transmitted light is only one half the saturation level due to variations of the laser beam and the transmittance of the pattern. In this case, as shown in FIG. 10, the level of part of the light incident on the pattern is amplified to 0.5. Again in this case, the shot noise level and noise level in the sensors and related analog circuits are denoted by $\Delta a$ and $\Delta b$, respectively. Here, the correction is made as:

$$(0.5+\Delta a)/(0.5+\Delta b)=1+(\Delta a-\Delta b)/(0.5+\Delta b)$$

Figure 11:
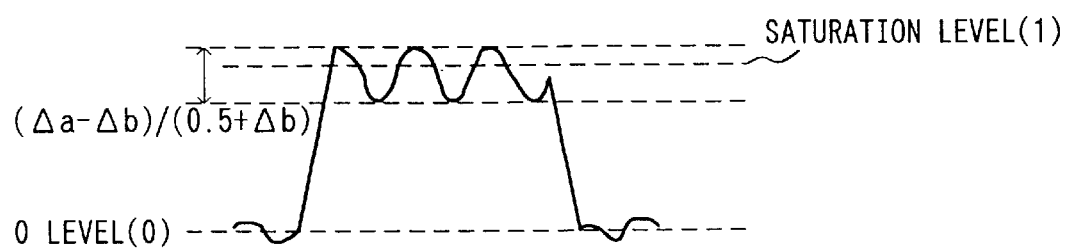
FIG. 11 shows the corrected output waveform.

As shown in FIG. 11, the corrected output signal has reached the saturation level, and the noise level is, from the above equation, $(\Delta a-\Delta b)/(0.5+\Delta b)$.

The difference in the noise level between the present invention and the above technique which was developed earlier by the inventor, resides only in whether the left term in the denominator in the left side of the equation representing the noise level is 1 or 0.5. However, while according to the present invention the "1" is always controlled to "1" as described before, according to the prior technique "0.5" represents the transmitted light level detected by the sensor, which is thus subject to variations with variations of the transmittance of the pattern and the laser beam level. Thus, according to the prior technique the noise level is affected by variations of the term "0.5" in the above equation and always subject to variations, whereas according to the present invention the noise level is always fixed. Likewise, according to the present invention the noise level of the edge signal is always fixed.

Also, comparison of the noise level according to the present invention and that according to the prior technique, performed by subtracting the former from the latter, i.e., $$(\Delta a-\Delta b)/((0.5+\Delta b)-(\Delta a-\Delta b)/(1+\Delta b)>0,$$

shows that the noise level is lower according to the present invention.

According to the two cases, the denominator is $(n+\Delta b)$ (n being 1 or below). When n is 1, $(\Delta a-\Delta b)/(n+\Delta b)$ has a minimum value. That is, according to the present invention the noise level is represented in the from that it is always minimum.

When the CPU 2 has calculated the noise level in the step S235, it calculates the necessary gain using the calculated noise level and supplies the calculated gain value to the gain setting means 7 (step S240, and also calculates the necessary offset and supplies the calculated offset value to the offset setting means 11 (step S245).

Figure 6:
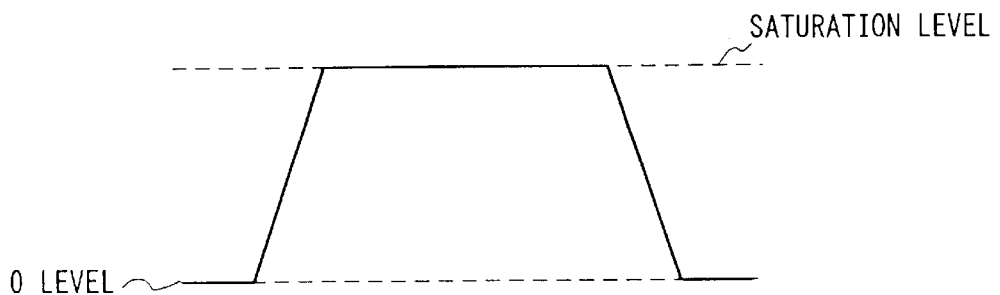
FIG. 6 shows relationship between the output of the sensor 6 and measurement limit of the A/D converter 12.
Figure 7:
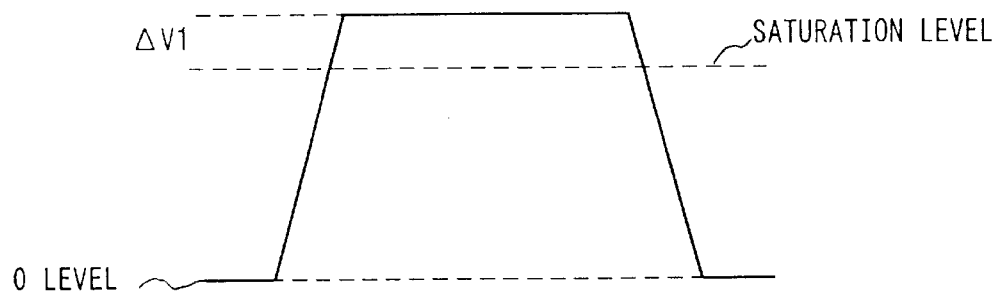
FIG. 7 shows the output waveform after correction according to the present invention.
Figure 8:
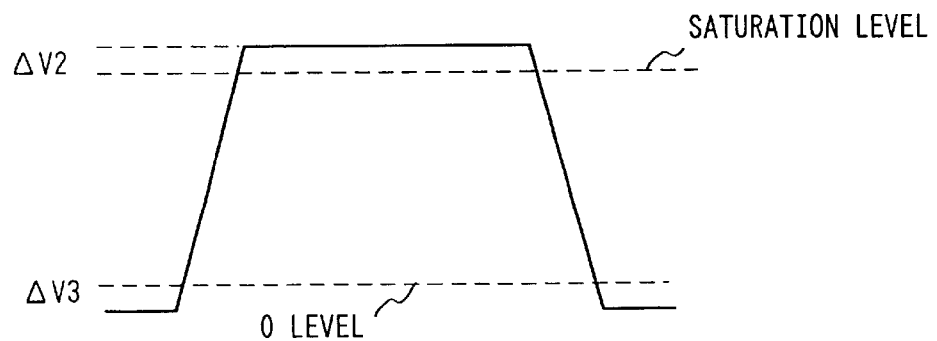
FIG. 8 represents the output waveform obtained by giving the offset to the waveform shown in FIG. 7.

The calculations of the gain and offset values will now be described with reference to FIGS. 6 to 8. In these Figures, saturation level and zero level are the upper and lower limits of measurement in the A/D converter 12. FIG. 6 shows the waveform of the signal representing the light transmitted through the pattern shown in FIG. 2. FIG. 7 shows the waveform of a signal obtained by dividing the signal waveform shown in FIG. 6 by the signal representing the branched light which is given the above gain. FIG. 8 represents the waveform obtained by giving the offset to the signal shown in FIG. 7.

Although the signals are shown by straight lines in the Figures for the sake of the brevity, these signals contain noises as described before.

Since the gain of the gain setting means 7 is 1 or below as noted above, division of the signal shown in FIG. 6 by the signal of the branched light with the gain given thereto produces a signal which is expanded as a whole as shown in FIG. 7, with an excess of $\Delta V1$ from the saturation level. When an offset of $-\Delta V3$ is given to this signal, the extent of excess from the saturation level is $\Delta V2$, as shown in FIG. 8.

Since a portion of signal in excess of the upper limit of measurement in the A/D converter is not measured, it is possible to remove the noise in that portion of signal if the noise level of the signal representing the light transmitted through the pattern is $\Delta V2$ or below. In addition, since a portion of signal at a level below the lower limit of measurement of the A/D converter is not measured, it is possible to remove the noise in that portion of signal if the noise level of the zero level signal is $\Delta V3$ or below.

In the above noise removal step, the offset value is thus calculated $\Delta V3$ and $\Delta V2$ are not below the noise level calculated in the step S235. Since the excess extents $\Delta v2$ and $\Delta v3$ are obtained with the excess extent $\Delta V1$, the gain is calculated to obtain expansion such that $\Delta V1$ is not less than $(\Delta V2+\Delta V3)$.

When the CPU 2 has calculated the gain and offset values, it instructs the A/D converter controller 14 to convert the analog signal to the digital signal (step S250), causes the digital signal data thus obtained to be stored as multiple-value data in the memory 13 (step S255). When the multiple-value data has been stored in the memory 13, the CUP 2 compares this data with desired pattern data which has been held beforehand in the memory 13 (step S260).

The operation of the embodiment having the construction as described above will now be described.

The user first sets the pattern to be shape checked in a predetermined position in the optical path noted above, and starts the check. When the check is started, the light source (not shown) is caused to emit a laser beam, and the CPU 2 causes control of the levels of the illuminating light and the branched light such that the detection levels detected by the sensors 6 and 5 are maximum detection level. After these output level control, the CPU 2 calculates the noise level, and then calculates the gain and offset values according to the result of the noise level calculation. The gain setting mean 7 gives gain to the analog signal from the sensor 5 according to the result of the gain and offset value calculations.

The correcting circuit 9, when receiving the analog signal obtained by giving the gain and the analog signal from the sensor 6, divides the analog signal from the sensor 6 by the analog signal obtained by giving the gain, and supplies the result to the offset setting circuit 10. The offset setting circuit 10, responsive to receipt of the output signal from the correcting circuit 9, receives the above offset value from the CPU 2, gives the offset to the signal received by the offset setting circuit 10, and supplies the signal obtained by giving the offset to the A/D converter 12.

When the A/D converter 12 receives this signal, the CPU 2 controls the A/D converter controller 14 to cause the A/D converter 12 to convert the analog signal to the digital signal and supply the digital signal to the memory 13. The memory 13, stores the same as multiple-value data. The CPU 2 compares this multiple-value data and desired pattern data stored beforehand in the memory 13 by visualizing these data on a display or a printer output medium.

The two data may be compared variously in dependence on the user's desired accuracy and purpose. Also, the comparison may be adequately modified; for instance, the difference between the two data may be recognized, and an alarm may be issued when the difference exceeds a predetermined threshold value.

As has been shown, since according to the present invention the laser beam is controlled to the maximum detection level of sensor, it is possible to make utmost use of the level detection ranges of the sensors even though the illuminating light level may be reduced. In addition, since the light transmitted through the pattern is normalized with the branched light, the laser beam output level variations are made up for, and noise present between the zero level and the saturation level is removed. Thus, data, in which the noise level of edge portions is always constant, is taken. It is thus possible to increase the accuracy and sharpness of the pattern image.

As has been described in the foregoing, according to the present invention the CPU can always take the data with constant noise level in the light transmitted through the pattern and edge detection data irrespective of changes in the sensor shot noise and analog circuit noise level, which may result from variations of the light transmitted through the pattern, laser beam level variations and sensor output variations in long use. Also, according to the present invention as claimed in claim 2, it is possible to obtain sharper and clearer images by reducing the noise level. Further, according to the present invention as claimed in claim 3, since noise can be partly removed, it is possible to obtain more accurate and shaper image. According to the present invention as claimed in claim 4, since noise other than those of edge portions can be removed, it is possible to obtain more accurate and sharper image. According to the present invention as claimed in claim 5, pattern recognition using a computer is conveniently obtainable. Moreover, according to the present invention claimed in claim 6, since the noise level is always fixed, it is possible to provide a pattern shape checking method, which permits ready noise removal.

Figure 13:
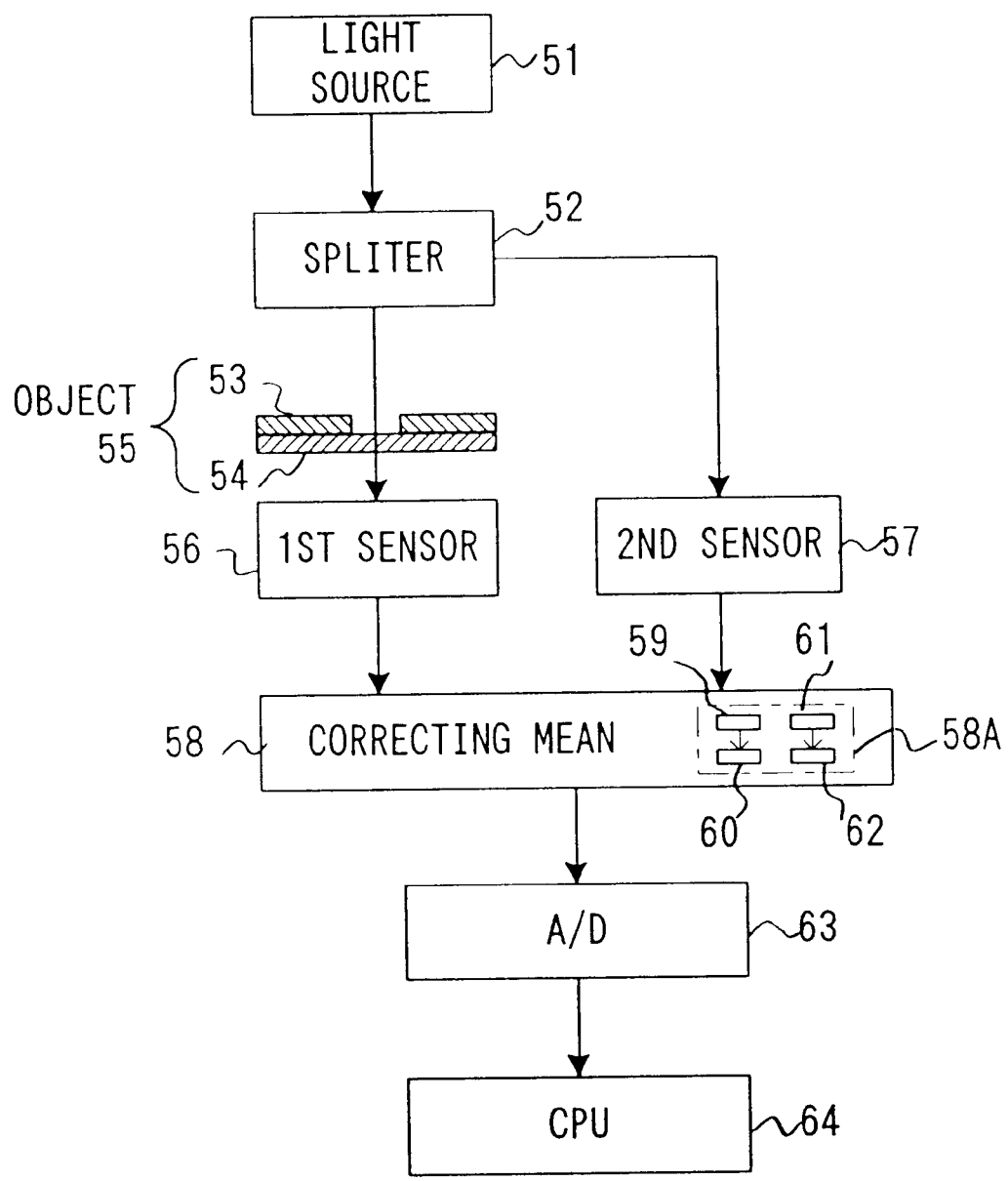
FIG. 13 shows a block diagram representation of the construction of the light-permeable area shape checking apparatus according to the present invention.

FIG. 13 is a block diagram representation of the construction of the light-permeable area shape checking apparatus according to the present invention. The illustrated light-permeable portion shape checking apparatus comprises a light source 51 for projecting checking light onto an object 55 to be checked, which has light-permeable areas transmitting light and light-blocking areas blocking light, a first sensor 56 for photoelectrically converting light transmitted from the light source 51 and transmitted through the light-permeable areas of the object 55, a correcting means 58 for correcting the output of the first sensor 51, an A/D converter 63 for converting the corrected sensor output supplied from the correcting means 58 to digital data, and a computing means (i.e., CPU) for shape checking the object according to the digital data from the A/D converter 63.

The object 55 usually has a mask pattern 53 and a light-permeable support 54 of glass or the like. The light-permeable areas of the object are areas of the support 54 exposed by notched portions (i.e., notches and holes) of the mask pattern 53, and the light-blocking areas are support areas covered by the mask pattern.

The correcting means 58 includes gain correcting means 58A, which converts the signal waveform of the first sensor output to make the maximum level thereof to be above upper limit of measurement of the A/D converter and also make the minimum level of the first sensor output to be below the lower limit of measurement of the A/D converter. Specifically, the gain correcting means 58A amplifies the first sensor output such that the maximum and minimum levels thereof are above the upper limit and below the lower limit of measurement of the A/D converter, respectively. Thus, the continuous light-permeable or light-blocking area portions of the first sensor output, may be set to the upper or lower limit of measurement of the A/D converter without sacrifice of the accuracy of the hole edge portions of the mask pattern or the like. It is thus possible to satisfactorily remove harmonic component noise superimposed on the signal.

The example shown in FIG. 13 shows two sensors, i.e., a first sensor 56 which photoelectrically converts the light projected from the light source and transmitted through the light-permeable areas of the object 55, and a second sensor 57 which photoelectrically converts the light projected from the light source 51. The correcting means 58 corrects the output of the first sensor 56 according to the output of the second sensor 57.

The correcting means 58 includes a ratio signal supplying means 59 for supplying a ratio signal representing the ratio between the outputs of the first and second sensors, and an amplifying means 60 for amplifying the waveform of the ratio signal such that the maximum and minimum levels thereof is above the upper limit and below the lower limit of measurement of the A/D converter, respectively. In this example, the ratio signal applying means 59 and the amplifying means 60 constitute a gain correcting means 58A.

For the harmonic (high frequency) component removal, the amplifying means 60 may suitably determine the signal amplification amplitude according to the amplitude of the harmonic component. In other words, the correcting means 60 amplifies the ratio signal such that the maximum and minimum levels thereof will be above the upper limit and below the lower limit of measurement of the A/D converter to predetermined extents. The predetermined extents are determined as follows. The harmonic component noise amplitude is amplified in dependence on the constructions of the analog circuit and sensor employed, and then the amplification factor for the waveform amplification is calculated such that the component exceeds the saturation and zero levels of the A/D converter 63.

To be able to cope with changes in the sensitivity of the sensor and changes in the light permeability of the glass support 54, the correcting means 58 includes a ratio calculating means 61 for calculating the ratio between the output level of the second sensor 57 and a reference level, and an output correcting means 62 for correcting the output of the first sensor with the calculated ratio. It is thus possible to correct the second sensor output level with the ratio calculated by the ratio calculating means 11 irrespective of light level changes with changes in the light permeability of the object under check. This means that by calculating the ratio between the first and second sensor outputs it is possible to sample the pattern without being adversely affected by the sensitivity of the sensor and the light permeability of the object.

In this embodiment, the sensor output signal which represents the detected light transmitted through the pattern, is corrected for saturation to a fixed level with a signal obtained by intentionally changing the gain of the sensor output signal which represents the detected laser beam, and also signal resulting when the laser beam is not transmitted through the pattern, is given an offset, thereby setting zero level for the absence of incident light.

Figure 14:
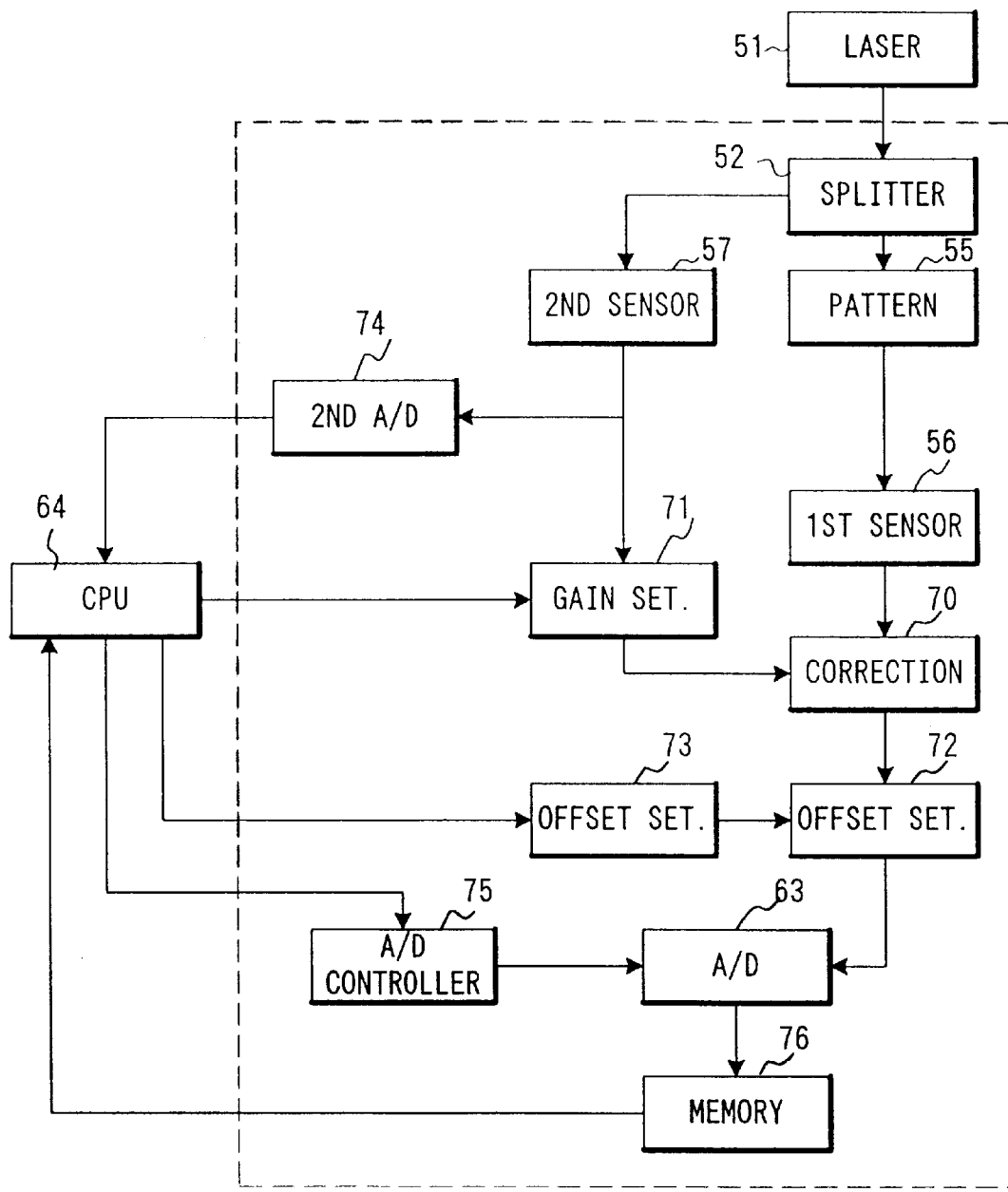
FIG. 14 shows a block diagram showing the construction of an embodiment of the present invention.

FIG. 14 is a block diagram showing the construction of an embodiment of the present invention. Here, a laser 51 for producing a laser beam spot is adopted as the light source. A beam splitting means 52 splits the laser beam projected from the laser 51 into two split laser beams, one being used to scan the pattern 55 of an object, the other being directed to a second sensor 57 or monitoring the power level of the laser beam. A first sensor 56 receives a transmitted laser beam from the pattern 55, and the second sensor 57 detects the power level of the projected laser beam. A CPU 74 receives a digital output of a second A/D converter 74, which A/D converts the output of the sensor 57.

In this embodiment, the second A/D converter 74 converts the output of the second sensor 57 to digital data, constitutes the amplifying means 60 shown in FIG. 13 together with a comparing means for comparing the output level of the second A/D converter 74, and a predetermined reference level, and a gain setting means 71 for reducing the output level of the second sensor 57 when this level is higher than the reference level while increasing the same level in the converse case. More specifically, the CPU 64 functions as part of the gain setting means 71 and the comparing means.

The CPU 64 supplies to the gain setting means 71 a command for setting the output level of the second sensor to a predetermined level. The gain setting means 71 provides a gain to the second sensor 57 in response to command from the CPU 64. As the gain setting means 71 may be used a variable amplifier capable of digitally setting data or a programmable attenuator.

A correcting circuit 70 supplies the ratio between the output level of the second sensor 57, to which the gain is set by the gain setting means 71, and the output level of the first sensor 56. In this way, low frequency components of the laser beam output of the laser 51 are removed. Also, with the provision of the above ratio, the CPU 64 always obtains a fixed value irrespective of laser beam power level variations. Specifically, an A/D converter 63 converts the output of the correcting circuit 70 to digital data, which is stored in a memory 76, and the CPU 64 can recognize the pattern shape not affected by laser beam power level variations by reading out the data stored in the memory 76.

In this embodiment, the amplifying means 60 further includes an offset setting means 73, which offsets the ratio signal from the ratio signal supplying means, with the gain set therefor by the gain setting means, in the upward or downward amplitude direction according to the gain set by the gain setting means. The offset setting means 73 gives an offset to an offset setting circuit 72 in response to a command from the CPU 64. The offset setting means 73 may set the offset by using a D/A converter or by voltage setting using a programmable resistor.

The A/D converter 63 A/D converts the output of the offset setting circuit 72 and stores the digital data thus produced in the memory 76 at a timing instructed from an A/D converter controller 64. The CPU 64 can recognize the pattern image from the data stored in the memory 76.

The correcting circuit 70 will now be described in detail. The correcting circuit 16 is usually a divider implementing an equation:

(Output of correcting circuit 70)=(Output of first sensor 56)/(Output of second sensor 57).

For example, when the outputs of the second and first sensors 57 AND 56 are a and b, respectively, the correcting circuit 70 provides an output of b/a. When the output of the second sensor 57 is reduced to a/2 with a laser beam output level reduction due to some or other cause, the output of the first sensor 56 is also reduced to b/2, but the output of the correcting circuit 56 remains to be b/a. This means that it is possible to obtain a constant corrected output irrespective of laser beam output variations. In this embodiment, the following equation (1) is further adopted.

(output of correcting circuit 70)=(Output of first sensor 56)/(Output of second sensor 57)×k  (1)

where k is the gain set in the gain setting means 71.

With this equation (1), the detected level of the light transmitted through the pattern 55 is saturated to a constant, which is above the upper limit of measurement of the A/D converter 61. Thus, the data of the measured light transmitted through the patter 55 is made to be the maximum output of the A/D converter 63. The offset setting circuit 52 also shifts the output of the correcting circuit 70 to a negative level. When the pattern 55 does not transmit the light, the measurement data is made to the minimum output level of the A/D converter 63 by making an output below the lower limit of measurement of the A/D converter 63. By using the equation (1), it is possible to obtain stable sampling data irrespective of laser beam level variations and sensor variations in long use.

Figure 15:
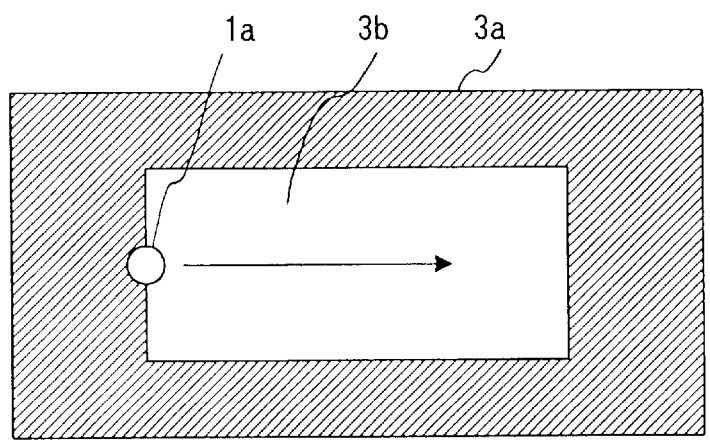
FIG. 15 shows a drawing representing manner of scanning of the pattern by the laser beam.
Figure 16:
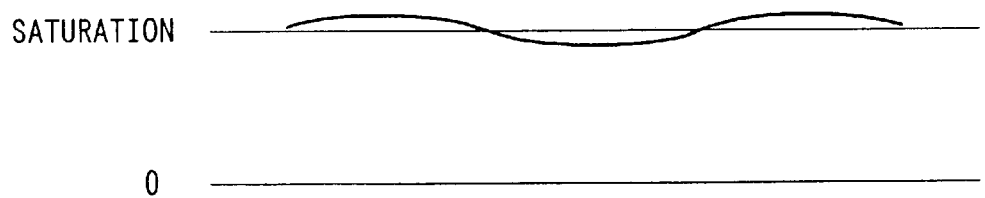
FIG. 16 shows a waveform diagram showing a waveform, which is obtained as a result of photoelectric conversion of the scanning with the beam spot by the second sensor 57.

The operation of the embodiment will now be described with reference to the illustration of actual waveforms. FIG. 15 shows a manner of scanning of the pattern by the laser beam. The object to be checked has a non-light-permeable area 3a and a light-permeable area 3b. The object is scanned by a beam spot 1a. FIG. 16 is a waveform diagram showing a waveform, which is obtained as a result of photoelectric conversion of the scanning with the beam spot by the second sensor 57. In FIG. 16 and following Figures, "0" and "Saturation" label the zero and saturation output levels of the A/D converter 63, respectively. The example of the output shown in FIG. 16 contains low frequency noise, and its direct A/D conversion produces the maximum output level of the A/D converter when it is higher than the saturation level, while producing multiple-data for its portions below the saturation level.

Figure 17:
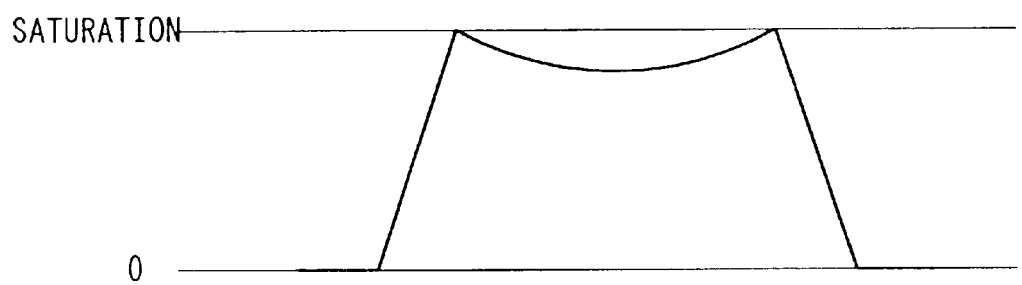
FIG. 17 shows the output of the first sensor 56 photoelectrically converting the light transmitted through the object shown in FIG. 14.

FIG. 17 shows the output of the first sensor 56 photoelectrically converting the light transmitted through the object shown in FIG. 14. In the example shown in FIG. 17, the low frequency component is added to the transmitted light because of the same light source. In FIGS. 16 and 17, the showing of the waveforms by bold lines means that harmonic component is added in the range of the bold line. The rising and falling portions shown in FIG. 17 are generated because the laser beam produces a circular spot. Specifically, the spot is first partly superimposed on the edge of the object, and the level is progressively increased from the zero level to the saturation level. The slanted rising and falling are compared as digital data with digital data obtained from the good product, whereby highly accurate check for edge defects can be obtained.

Figure 18:
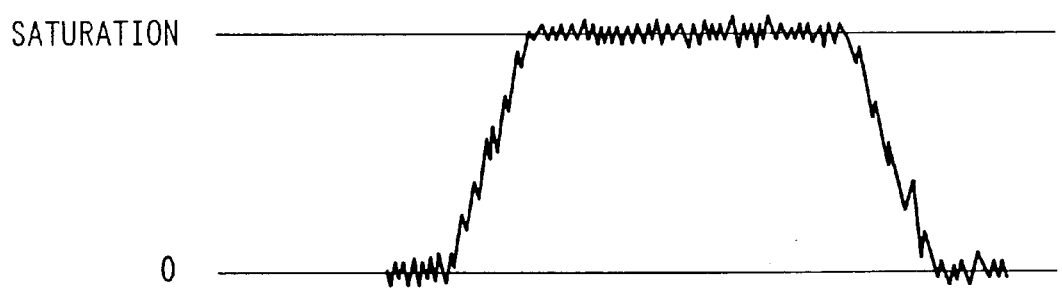
FIG. 18 shows the waveform containing remaining harmonic component striding the saturation.

The correcting circuit 70 executes the division of the waveform b shown in FIG. 17 by the waveform a shown in FIG. 16, thus obtaining a waveform as shown in FIG. 18. In FIG. 18, the harmonic component is actually shown instead of replacing it with a bold line. By taking this ratio, it is possible to remove the noise contained in the light from the light source itself and also noise component which is common to both the sensors. The waveform shown in FIG. 18, however, contains remaining harmonic component striding the saturation or zero level.

In this embodiment, the remaining harmonic component is removed by adding the gain to the waveform shown in FIG. 18. First, the gain of the gain setting means is set to 1. Assuming the outputs of the second and first sensors 57 and 56 to be a and b, respectively, the output of the correcting circuit 70, having the waveform as shown in FIG. 18, is given by the following equation (2).

$$\text{(Output of correcting circuit 70)} = b/a \qquad (2)$$

Referring to FIG. 18, the saturation and zero levels are made to be the upper and lower limits of measurement of the A/D converter 63. In this case, the measurement shown in FIG. 15 usually contains measurement errors in the A/D converter, sensor shot noise and analog circuit noise.

Figure 19:
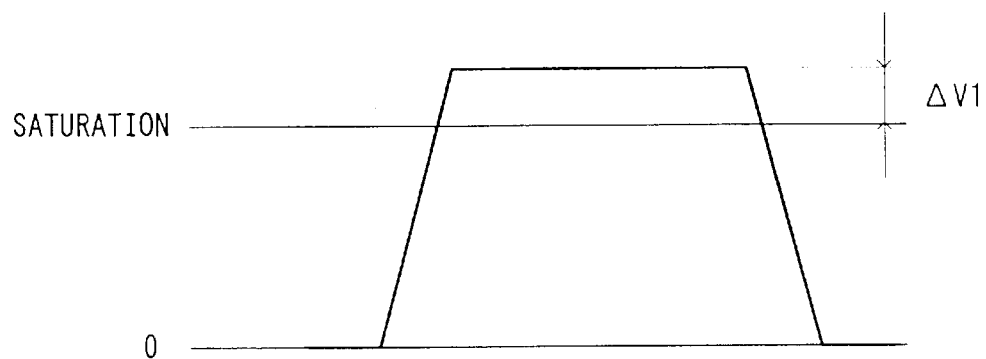
FIG. 19 shows an amplified waveform with the gain shown in FIG. 18.

When the output of the second sensor 57 is changed by the gain setting means 71 to 0.8a when the output of the first sensor 56 is b, the correcting circuit 70 provides an output having an waveform as shown in FIG. 19, which is given by the following equation (3).

$$\text{(Output of correcting circuit 70)} = b/0.8a = b/a + \Delta V1 \qquad (3)$$

Figure 20:
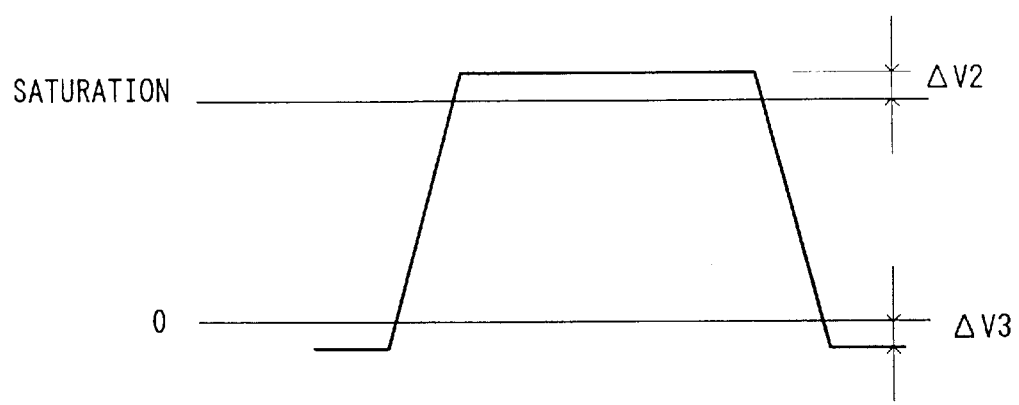
FIG. 20 shows a waveform shifted in the downward direction shown in FIG. 19.

An offset of $-\Delta V3$ is then set in the offset setting means 73, whereby the offset setting circuit 72 adds the offset of $-\Delta V3$ to the output of the correcting circuit 70. FIG. 20 is a waveform diagram showing the waveform of the output of the offset setting circuit 72. The A/D converter 63 converts this waveform to digital data, which is stored in the memory 76. The stored data is the maximum level of measurement of the A/D converter when it is above the saturation level and the minimum level of measurement of the A/D converter when it is below the zero level.

Referring to FIG. 20, the CPU 64 thus sets $\Delta V1$ and $\Delta V3$ such that $\Delta V2$ is above the maximum level of the A/D converter 63 and $Av3$ is below the minimum level of the A/D converter, and thus it can obtain a pattern signal free from measurement errors in the A/D converter 63, sensor noise and analog circuit noise. Since $\Delta V1 = \Delta V2 + \Delta V3$, the harmonic component amplitude may be experimentarily measured, and the gain may be added to the waveform such as to more than double the measurement.

A sensor output increase by 4/5 times, i.e., to 0.8b, due to a change in the output of the first sensor 56 due to long use and also a change in the light permeability of the glass 54 of the object to be checked, can be detected as follows. The A/D converter 63 converts the light-permeable portion output of the first sensor to digital data, which is stored in the memory 76. The CPU 64 then compares a predetermined reference level stored in the memory 76 and the output level of the first sensor, and takes the ratio between these two levels. The change in the first sensor output can be detected from this ratio.

For example, when the output of the first sensor 56 is changed by 4/5 times, the CPU 64 causes the gain setting means 71 to change the output signal of the second sensor 57 by 4/5 times. In this case, the output of the correcting circuit 70 is as shown by the following equation (4).

$$\text{(Output of correcting circuit 70)} = 0.8b/0.8a = b/a \qquad (4)$$

Thus the waveform shown in FIG. 18 can be obtained as stable waveform irrespective of changes in the sensitivity of the sensors in long use or changed in the light permeability of the pattern.

As has been described in the foregoing, with the above embodiment the CPU can take the detected level of light transmitted through the pattern 55 always as a constant level irrespective of changes in the sensors, changes of the analog circuits in long use, and changes in the light permeability of the pattern. In addition, in the detection of the light transmitted through the pattern 55, the CPU can take a detected level free from measurement errors in the A/D converter, sensor shot noise and analog circuit noise. Furthermore, in the detection of the laser beam not transmitted through the pattern 55, the CPU can take a detected level free from errors in the A/D converter 63, sensor shot noise and analog circuit noise.

Thus, when sampling the pattern using the laser beam, the CPU can obtain a stable and sharper pattern image. It is thus possible to permit pattern shape check with a construction which is simple compared to the prior art construction. Besides, since the gradation values of the light-permeable and non-light-permeable portions are made to upper and lower limits of the A/D converter, respectively, it is possible to obtain a faster and stabler pattern shape check process.

With the construction as described above according to the present invention, the gain correcting means corrects, by changing the output signal waveform of the first sensor, the maximum output level of the first sensor to be above the upper limit of measurement of the A/D converter and the minimum output level of the first sensor to be below the lower limit of measurement of the A/D converter. Thus, when the slope of rising and falling portions becomes slightly sharper, the maximum and minimum levels of the first sensor may be made to get out of the capacity of the A/D converter, thus obtaining monotonous data after the A/D conversion. It is thus possible to obtain a unique and excellent light-permeable portion shape checking apparatus, which provides a maximum or a minimum digital data value with object portions, which have continuous light-permeable or non-light-permeable areas and are not so important for the pattern shape check, thus permitting pattern sampling image capable of being readily processed and improving the accuracy of the pattern shape check, permits high speed processing, and further permits generation of a stable satisfactory pattern sampling data and stable pattern shape check irrespective of changes in the sensitivity of sensor or the like due to long use.

Changes in construction will occur to those skilled in the art and various apparently different modifications and embodiments may be made without departing from the scope of the present invention. The matter set forth in the foregoing description and accompanying drawings is offered by way of illustration only. It is therefore intended that the foregoing description be regarded as illustrative rather than limiting.

What is claimed is:

1. A light-permeable portion shape checking apparatus comprising a light source for emitting checking light illuminating an object to be checked, the object having light-permeable areas transmitting light and light-blocking areas blocking light, a first sensor for photoelectrically converting light emitted from the light source and transmitted through the light-permeable portions of the object, a second sensor for photoelectrically converting the illuminated light from the light source, correcting means for correcting the output of the first sensor on the basis of the output of the second sensor, an analog-to-digital converter for converting the corrected sensor output from the correcting means to digital data, and computing means for shape checking the object according to the digital data from the analog-to-digital converter, the correcting means including a ratio signal supplying means for supplying a ratio signal representing the ratio between the output signals of the first and second sensors, and an amplifying means for amplifying the waveform of the first sensor output signal such that the maximum and minimum levels of the ratio signal are above the upper limit and below the lower limit of the analog-to-digital converter, respectively.

2. The light-permeable portion shape checking apparatus according to claim 1, wherein the amplifying means includes means for amplifying the ratio signal such that the maximum and minimum levels of the ratio signal are above the maximum level and below the minimum level of the analog-to-digital converter to predetermined extents, respectively.

3. The light-permeable portion shape checking apparatus according to claim 1, wherein the amplifying means includes a second analog-to-digital converter for converting the output of the second sensor to digital data, comparing means for comparing the output level of the second sensor, provided by the second analog-to-digital converter, and a predetermined reference level, and output setting means for reducing the output level of the second sensor when it is found by the comparing means that the output level of the second sensor is higher than the reference level, while increasing the output level of the second sensor when it is found that the output level of the second sensor is lower than the reference level.

4. The light-permeable portion shape checking apparatus according to claim 3, wherein the amplifying means includes an offset setting means for providing an offset to the ratio signal output of the ratio signal supplying means, provided with the gain set by gain setting means, either upward or downward in the amplitude direction according to the extent of the gain that has been set.

5. A light-permeable portion shape checking method comprising steps of:

emitting checking light illuminating an object to be checked, the object having light-permeable areas transmitting light and light-blocking areas blocking light;

photoelectrically converting light emitted from light source and transmitted through the light-permeable portions of the object by a first sensor;

photoelectrically converting the illuminated light from the light source by a second sensor;

amplifying the waveform of the first sensor output signal such that the maximum and minimum levels of a ratio signal representing the ratio between the output signals of the first and second sensors are above the upper limit and below the lower limit of an A/D converter, respectively;

converting the corrected output from the correcting means to digital data by the A/D converter; and shape checking the object according to the converted digital data.

* * * * *

UNITED STATES PATENT AND TRADEMARK OFFICE
CERTIFICATE OF CORRECTION

PATENT NO. : 6,326,606 B2  
DATED : December 4, 2001  
INVENTOR(S) : Katsunori Nagamatsu Page 1 of 1

It is certified that error appears in the above-identified patent and that said Letters Patent is hereby corrected as shown below:

Column 16,  
Line 1, delete "Av3" insert -- AV3 --

Signed and Sealed this

Twenty-eighth Day of May, 2002

Attest:

JAMES E. ROGAN  
*Attesting Officer*   *Director of the United States Patent and Trademark Office*